United States Patent [19]

Rashkin

[11] 4,208,539

[45] Jun. 17, 1980

[54] HYDROGENATION OF ACETOPHENONE USING BARIUM-COPPER CHROMITE-ZINC

[75] Inventor: Jay A. Rashkin, Piscataway, N.J.

[73] Assignee: Halcon Research and Development Corporation, New York, N.Y.

[21] Appl. No.: 35,886

[22] Filed: May 4, 1979

Related U.S. Application Data

[62] Division of Ser. No. 908,610, May 23, 1978, Pat. No. 4,160,746.

[51] Int. Cl.$^2$ ............................................. C07C 31/14
[52] U.S. Cl. .................................................... 568/814
[58] Field of Search ......................................... 568/814

[56] References Cited

U.S. PATENT DOCUMENTS

| | | | |
|---|---|---|---|
| 2,125,412 | 8/1938 | Arnold et al. | 252/468 |
| 2,137,407 | 11/1938 | Lazier | 568/814 |
| 2,544,756 | 3/1951 | Guest et al. | 568/814 |

OTHER PUBLICATIONS

Adkins et al., "J. Am. Chem. Soc." 53 (1931) pp. 1091-1095.
Conner et al., "J. Am. Chem. Soc." 54 (1932) pp. 1138-1145.

Primary Examiner—Joseph E. Evans
Attorney, Agent, or Firm—William C. Long; David Dick; Harold N. Wells

[57] ABSTRACT

A catalyst for the liquid phase hydrogenation of acetophenone to phenyl methyl carbinol having improved physical strength and superior selectivity to the desired product having a composition expressed as oxides consisting essentially of: (a) a barium-copper chromate containing 30–55 wt. % CuO, 30–57 wt. % $Cr_2O_3$, and up to 16 wt. % BaO; and (b) 1–13 wt % ZnO relative to 100% by weight of said barium-copper chromite. In a preferred embodiment 0.15–1.7 wt. % MgO relative to 100% by weight of said barium-copper chromite is included. The zinc compound may be added by solution impregnation of the barium-copper chromite or as a powder. Preferably, the catalyst is prepared by combining into a wet paste a barium-promoted copper chromite and a zinc compound and preferably also magnesium chromate, followed by drying the paste and then calcining the dried mixture. After calcination, the catalyst typically is pelletized for use in a fixed bed reactor. The magnesium chromate may be added directly to the mixture as the powdered compound. Alternatively, stoichiometric quantities of magnesium oxide and chromium trioxide may be prepared in an aqueous solution.

2 Claims, No Drawings

HYDROGENATION OF ACETOPHENONE USING BARIUM-COPPER CHROMITE-ZINC

This is a division of application Ser. No. 908,610 filed May 23, 1978 now U.S. Pat. No. 4,160,746.

PRIOR ART

The invention relates generally to a catalyst for the hydrogenation of aromatic ketones to alcohols. More particularly, the invention relates to an improved catalyst for the hydrogenation of acetophenone to phenyl methyl carbinol (methyl benzyl alcohol).

Hydrogenation of acetophenone to phenyl methyl carbinol has been of particular commercial interest, since styrene may be obtained by dehydration of phenyl methyl carbinol (see U.S. Pat. No. 3,526,674). The phenyl methyl carbinol may be obtained by oxidation of ethyl benzene, as suggested in the prior art, or as a by-product in the preparation of propylene oxide by reaction of propylene with ethyl benzene hydroperoxide (see U.S. Pat. Nos. 3,351,635 and 3,350,422).

Catalysts for carrying out such hydrogenations have been known for many years. Brochet in U.S. Pat. No. 1,247,629 disclosed the use of catalytic metals having an atomic weight between 55 and 59, such as nickel, cobalt, iron, etc. for the hydrogenation of acetophenone. Ipatieff, et al., in U.S. Pat. No. 2,334,100, disclosed a method for hydrogenating alkyl aryl ketones, including acetophenone, with a composite catalyst comprising copper, zinc and alumina.

The general application of copper chromite catalysts to the hydrogenation of an unsaturated oxygen to carbon linkage, including the conversion of ketones to alcohols, is disclosed in U.S. Pat. No. 2,137,407 to Lazier. In Example 3, the patentee disclosed a method for preparing a barium-modified copper chromite catalyst by the precipitation of barium-copper ammonium chromate from aqueous solutions of barium and copper nitrates using ammonium bichromate and ammonium hydroxide. In U.S. Pat. No. 2,125,412, granted to Arnold, et al., such copper chromite catalysts, with and without barium, are disclosed for use in the hydrogenation of the keto group of an aromatic ketone having at least three benzene rings.

A group of patents assigned to Union Carbide and Carbon Corporation, and concerned with the process for hydrogenation of acetophenone to phenyl methyl carbinol, include U.S. Pat. Nos. 2,544,756, 2,554,771, 2,575,403, and 2,575,404. These patents relate particularly to improvement of the copper-chromium catalysts, which had been successfully used in such hydrogenations.

More recently, patents issued to Grane, et al., and assigned to the Atlantic Richfield Company, specifically, U.S. Pat. Nos. 3,927,120 and 3,927,121, disclosed the use of copper metal dispersed in a zinc oxide matrix as a catalyst for hydrogenation of acetophenone to phenyl methyl carbinol. The patents disclose a preferred catalyst composition and also that certain diluents had been found to provide improved conversion and selectivity to the hydrogenation reaction.

It should be noted that the hydrogenation of acetophenone is preferably carried only so far as to produce the corresponding alcohol, that is phenyl methyl carbinol. However, excessive hydrogenation will produce ethyl benzene, which has less value than the alcohol since the ethyl benzene must be reoxidized to the alcohol for conversion to styrene. Accordingly, it is desirable to produce phenyl methyl carbinol with a minimum of ethyl benzene, that is, with high selectivity to the production of phenyl methyl carbinol.

It has been found that pellets of copper in a zinc oxide matrix, when used for the hydrogenation of liquid acetophenone, rapidly lose both activity and physical strength and consequently require early replacement. A catalyst having both higher physical strength, along with improved selectivity to the production of phenyl methyl carbinol has been needed. Also, copper chromites, which have also been used for the hydrogenation of acetophenone, have been considered to have relatively inferior strength in the pellet form (see for example U.S. Pat. Nos. 3,256,208 and 3,235,514) and a stronger pellet than can be made solely with copper chromites would be preferred for fixed bed hydrogenation.

Two patents of interest with regard to the method of catalyst preparation to be discussed in detail hereinafter are U.S. Pat. Nos. 3,256,208, assigned to Japan Gas Chemical Company, and 3,840,478, assigned to Mitsubishi Gas Chemical Company. Both patents relate to the preparation of catalysts especially suited for the production of methanol carried out in the gas phase by reacting carbon monoxide and hydrogen. The patents disclose and claim catalysts which are produced by combining a pyrolyzed copper ammonium chromate (copper chromite) with chromium trioxide and zinc, in the '478 patent as zinc carbonate and as zinc oxide, zinc acetate, and zinc hydroxide in the '208 patent. The catalyst of the '478 patent includes additional copper in the form of basic copper carbonate.

An improved catalyst has now been found for hydrogenating acetophenone to phenyl methyl carbinol with high selectivity to the desired product and having a substantially higher physical strength after exposure to the liquid phase reaction than the copper-zinc oxide catalyst used heretofore.

SUMMARY OF THE INVENTION

A catalyst for the liquid phase hydrogenation of acetophenone to phenol methyl carbinol consists essentially of a barium-promoted copper chromite catalyst formulated with a zinc compound, typically zinc nitrate and preferably with the addition of magnesium chromate.

The barium-promoted copper chromite may be prepared by coprecipitating the barium, copper, and chromium as a copper ammonium chromate from an aqueous solution of barium and copper nitrates by the addition of ammonium bichromate and ammonium hydroxide. Alternatively, other known methods of preparing copper chromite catalysts may be employed. A powdered barium-promoted copper chromite is obtained by drying the precipitated barium-copper ammonium chromate and then calcining at a temperature in the range of 250° to 400° C., preferably about 340°–370° C., in the presence of air.

The calcined barium-copper chromite powder may be solution impregnated with the zinc compound. Preferably, the calcined barium-copper chromite powder is combined with the magnesium chromate and/or zinc compound, in the form of a wet paste. The paste is dried at a temperature in the range of 50°–200° C., preferably 140°–180° C., to remove substantially all the moisture and then calcined at a temperature of about 200°–400° C. in air, preferably about 225°–350° C. The catalyst is finished by crushing it to fine granules, preferably about 20–30 mesh (Tyler) in size, and then pelletizing the granules with a small amount of graphite, or other lubricant, to the size desired for use in a fixed bed reactor.

The magnesium chromate may be, either dry blended as a powder with the barium-copper chromite and the zinc compound, and the dry blended powders thereafter formed into a wet paste, or alternatively, the magnesium chromate may be formed by combining aqueous solutions of stoichiometric quantities of magnesium oxide and chromium trioixde, followed by the addition of the zinc compound, and thereafter adding the solution to the barium-copper chromite.

The finished catalyst will contain: (a) a barium-copper chromite having a composition expressed as the oxides about 30–55% by weight CuO, 30–57% by weight $Cr_2O_3$, and up to 16% by weight BaO; and (b) 1–13% by weight ZnO, relative to 100% by weight of said barium-copper chromite. MgO may be included in an amount 0.15–1.7% by weight relative to 100% by weight of said barium-copper chromite. Preferably, the composition will contain a barium-copper chromite having a composition of about 40–45% by weight CuO, 40–47% by weight $Cr_2O_3$, and 8–12% by weight BaO, and 2.5–7.5% by weight ZnO, and 0.5–1.2% by weight MgO relative to 100% by weight of said barium-copper chromite.

The catalyst has improved selectivity and physical strength relative to prior art catalysts in the liquid phase hydrogenation of acetophenone to phenyl methyl carbinol at temperatures in the range of 50° to 200° C., pressures in the range of 20 to 140 kg/cm$^2$ gauge, and where at least one mol of hydrogen is used for each mol of acetophenone.

DESCRIPTION OF THE PREFERRED EMBODIMENTS

The catalyst of the invention is intended particularly for use in the liquid phase hydrogenation of acetophenone to phenyl methyl carbinol. The reaction can be carried out by passing the liquid feed through a reaction vessel into which hydrogen gas is sparged and where the reactants are contacted with the catalyst in a powdered form. Such a method is termed a slurry reaction, since the catalyst is slurried in the reacting mixture. However, the disadvantages of a slurry reaction make the use of a fixed bed of catalyst desirable. For use in a fixed bed, the catalyst must be formed into pellets to provide passages for the reactants through the bed. As previously noted, it has been found that the copper-zinc oxide catalyst of the prior art has inferior strength when used in a fixed bed, and a stronger catalyst having improved performance has been desired. Also, copper chromites are known to have relatively low strength and a stronger pellet than is made solely with copper chromites has been sought.

Catalyst Composition and Preparation

Broadly, the catalyst of the invention will contain the metals copper, chromium, barium, zinc, and magnesium and, when expressed as the equivalent oxides, will have a composition consisting essentially of: (a) a barium-copper chromite containing 30–55% by weight CuO, 30–57% by weight $Cr_2O_3$, and up to 16% by weight BaO; and (b) 1–13% by weight ZnO relative to 100% by weight of said barium-copper chromite. Alternatively, the composition may include 0.15–1.7% by weight of MgO relative to 100% by weight of said barium-copper chromite. Preferably, the catalyst composition expressed as the equivalent oxides is: (a) a barium-copper chromite containing 40–45% by weight CuO, 40–47% by weight $Cr_2O_3$, and 8–12% by weight BaO; and (b) 2.5–7.5% by weight ZnO, and 0.5–1.2% by weight of MgO relative to the 100% by weight of the barium-copper chromite. Preferably, some barium will be present since it is known to be a promoter for copper chromite, although the amount of barium used may be varied substantially as will be evident from the broad range shown. It will be understood that the metals are expressed as specific oxides for convenience and precision in defining the composition ranges, rather than as a statement of the actual form in which the metals appear in the finished catalyst or in use. As prepared, the catalyst of the invention includes a barium-copper chromite, which is a recognized composition whose chemical formula may vary depending on the amounts of reactants. When a zinc compound and magnesium chromate are added to the barium-copper chromite and the mixture calcined in air, the resulting catalyst is presumed to contain each of the metals in an oxidized form, but the precise composition is not known. Later, when the catalyst is exposed to hydrogenation conditions, it is presumed that at least the copper content will be partially to fully reduced to the metallic form. Accordingly, compositions given herein are based on the equivalent metal oxides to avoid ambiguity and for consistency of expression.

The first step in preparing the catalyst of the invention is to form a barium-promoted copper chromite catalyst powder, generally by methods similar to those known in the prior art. One method of preparing such a copper chromite catalyst powder is to dissolve appropriate amounts of copper nitrate trihydrate and barium nitrate in distilled water and to precipitate a barium-copper ammonium chromate by the addition of a solution of ammonium bichromate and ammonium hydroxide. The precipitate is filtered out of the solution, washed in distilled water and dried at a temperature which would generally be above 100° C., typically about 110° C. After drying, the catalyst powder is then calcined in the air in the range of 250° to 400° C., preferably about 340°–370° C., for at least two hours in order to convert the barium-copper ammonium chromate to an active barium-promoted copper chromite catalyst.

Alternatively, barium-copper chromite powder could be produced by other methods known in the art and described in references which have been cited previously, as for example, precipitating copper, chromium, and barium from their nitrates or other salts by the use of carbonates.

Following the preparation of the barium-copper chromite catalyst powder, it may be activated, if desired, by treatment with an aqueous acetic acid solution, typically containing about 10% acetic acid, followed by washing with distilled water and drying at a temperature about 100° C. or above. Such acetic acid contacting has been found to increase the catalytic activity of such chromite catalyst powders (see for example U.S. Pat. No. 1,746,783).

After having prepared the barium-promoted copper chromite catalyst powder, other ingredients are added in order to produce a finished catalyst, normally in the form of pellets, since strong pellets have been particularly desired, although the catalyst could be used in the powder form in a slurry reaction if desired. As will be seen, a zinc compound is added to improve selectivity of the catalyst to the production of phenyl methyl carbinol. This may be done by solution impregnation of pellets formed from the barium-copper chromite, but preferably, the zinc compound is added in combination with magnesium chromate. The specific form in which zinc is added is not critical, but may be in any form which can be decomposed during the calcination of the finished catalyst to produce zinc in the oxide form. Typically, this will be in the form of a water soluble zinc salt such as a nitrate, acetate, hydroxide, carbonate-hydroxide, and the like.

At least two procedures have been found to produce a satisfactory catalyst pellet. The first procedure may be termed a "dry blending" technique, whereas the second procedure begins with an aqueous solution. In both methods, however, a wet paste is formed, which is then dried and calcined to produce the finished powder for pelletizing.

In the first method, the barium-copper chromite powder is dry mixed with a sufficient amount of magnesium chromate, $MgCrO_4$, to provide about 0.15 to 1.7% by weight of MgO in the finished catalyst, and sufficient zinc, typically in the form of zinc nitrate hexahydrate, to provide about 1 to 13% by weight zinc oxide in the finished catalyst. After dry blending, sufficient water is added to produce a wet paste that is thoroughly kneaded in order to produce a uniform mixture. Following the mixing process, the wet paste is dried at a temperature in the range of 50°–200° C., preferably 140° to 180° C., for a sufficient period of time in order to remove substantially all of the free water. This step normally will take up to about three hours to carry out, but typically two hours often has been found to be sufficient.

After completing the drying process, the catalyst is calcined at a temperature of about 200°–400° C. in air, preferably about 225°–350° C., for a sufficient period of time to convert the dried catalyst to an active form. Typically, about three hours will be sufficient. The claimed catalyst is then granulated by passing it through a 20–30 mesh (Tyler) sieve in order to produce a uniform particle size for introduction into conventional pelletizing equipment. Generally about 2% graphite, or other lubricant, is added to the catalyst particles to assist the pelletizing. The catalyst pellets may be of any suitable size, but typically will be cylinders about 3/16" (4.76 mm) diameter by ⅛" (3.175 mm) thick. The pellets preferably will have a crush strength of 35±5 lbs (15.9±2.27 kg). It may be noted that the use of higher pressure will produce pellets having higher crush strength, but at the expense of reduced available surface area. Lower crush strengths are undesirable since weaker pellets will tend to fracture under the stresses imposed by flow of reactants and the weight of the bed.

Since it is important that the catalyst retain its strength over a long period of exposure to reaction conditions, measurement of its crush strength is an important indication of the performance of the catalyst. Crush strength as reported herein has been carried out by the following method, and the results are reported as the pounds required to crush individual pellets. Individual pellets are placed in a universal test stand, Model LTCM, produced by John Chatellon & Sons, Kew Gardens, New York. Force is applied by the testing machine gradually and at a constant rate diametrically to the pellet against a spring-loaded indicator. When the pellet fractures, releasing the force, the indicator is locked at its maximum value, which is read as the crush strength of the pellet being tested.

In an alternative method of preparation, magnesium chromate is not added as the compound as done in the previous method. Instead, the magnesium chromate is first prepared by chemically reacting stoichiometric quantities of magnesium oxide and chromium trioxide in water to produce an amount of magnesium chromate in solution equivalent to that dry blended in the first procedure. To the magnesium chromate solution is added the desired amount of zinc compound and then the combined solution is mixed into the barium-copper chromite powder, along with added distilled water if necessary, to form a wet paste which is mixed, dried, and calcined in the same manner as previously discussed.

Method of Use

Catalyst pellets prepared according to the methods previously described have been found to provide improved results in the liquid phase hydrogenation of acetophenone to phenyl methyl carbinol. It is typical that such reactions are carried out under conditions which favor formation of phenyl methyl carbinol and minimize production of ethyl benzene. Temperatures will range between about 50° C. to 200° C., and typically will be between 135° C. and 155° C. The pressure will generally be between about 20 kg/cm² gauge to 140 kg/cm² gauge and typically about 80 kg/cm² gauge. The amount of hydrogen used is not critical. At least one mol of hydrogen will be used for each mol of acetophenone, but typically from about 1 to about 10 mols of hydrogen will be fed for each mol of acetophenone fed.

In a commercial operation, it would be expected that acetophenone would be diluted, as is disclosed in the Grane patents, to improve activity and selectivity to the desired product, phenyl methyl carbinol. For example, a typical feed would include about 20 to 60% by weight acetophenone in other hydrocarbons such as ethyl benzene, benzene, toluene, styrene, pseudo cumene, and the like.

It has been found that the addition of zinc to barium-copper chromite substantially improves selectivity of the hydrogenation of acetophenone and thus reduces the production of ethyl benzene. This effect is shown in the following example.

EXAMPLE 1

A barium-copper chromite catalyst is prepared by dissolving a suitable amount of copper nitrate trihydrate and barium nitrate in distilled water at 70° C. and then adding a solution of a suitable amount of ammonium bichromate dissolved in distilled water and mixed with 28% ammonium hydroxide solution in order to precipitate barium-copper ammonium chromate. The precipitate is filtered from the solution washed with distilled water, dried at 110° C. and then calcined for two hours at 360° C. to produce a barium-copper chromite containing 45 weight % CuO, 45 weight % $Cr_2O_3$, and 10 weight % BaO. The catalyst powder is pelleted with 2% graphite to produce pellets having a crush strength of about 30±5 lbs (13.6±2.27 kg). A portion of the pellets is impregnated with an aqueous solution of zinc nitrate hexahydrate and then dried at 110° C. for two hours, followed by calcining at 250° C. for three hours in air. The zinc-impregnated catalyst pellets contained about 3.4 weight % ZnO based on the barium-copper chromite pellets.

Both the zinc-impregnated pellets and some without zinc are placed in batch reactors and contacted with acetophenone and hydrogen at a temperature of 135° C. and 84 kg/cm² gauge. For each gram of catalyst, four (4) standard liters per hour of hydrogen gas are passed through a liquid charge of 34 grams containing 46.5 weight % acetophenone, 44.8 weight % pseudo cumene, 8.4 weight % phenyl methyl carbinol, and 0.3 weight % ethyl benzene for about four hours, at which time the acetophenone has been substantially converted to phenyl methyl carbinol.

The performance of the two catalysts is shown in Table I.

TABLE I

|  | ACTIVITY g/mols ACP/hr/cc cat | SELECTIVITY Mol % ACP Converted to BB @ 50% ACP Conversion |
|---|---|---|
| Ba-Cu Chromite | 0.039 | 4.3 |
| Ba-Cu Chromite + Zn | 0.026 | 1.1 |

It can be seen that the activity of the catalyst is reduced by the addition of zinc, but that a four-fold improvement in selectivity was obtained, which would be a very important advantage in commerical hydrogenation of acetophenone.

EXAMPLE 2

A catalyst is prepared according to the procedure of Example 1 to produce a barium-copper chromite catalyst powder containing about 45 wieght % CuO, 45 weight % Crhd 2O₃, 10 weight % BaO. The basic powder is dry blended with 3.1 weight % magnesium chromate powder and 24.4 weight % zinc nitrate hexahydrate powder. Sufficient water is added to form a wet paste, which is thoroughly kneaded and than dried at 170° C. for two hours in air, followed by calcination at about 250° C. for three hours in air. The calcined catalyst is then granulated through a 20–30 mesh sieve and pelletized along with 2% graphite to produce pellets 3/16" diameter by ⅛" thick, having an initial crush strength of about 35±5 lbs (15.9±2.27 kg).

The catalyst pellets are placed in a batch reactor for contact with acetophenone and hydrogen at a temperature of 135° C. and 84 kg/cm² gauge. For each gram of catalyst, four (4) standard liters per hour of hydrogen gas are passed through a liquid charge of 34 grams containing 46.5 weight % acetophenone, 44.8 weight % pseudo cumene, 8.4 weight % phenyl methyl carbinol, and 0.3 weight % ethyl benzene for about four hours, at which time the acetophenone has been substantially converted to phenyl methyl carbinol.

Calculation of the performance of the catalyst as prepared about (B) is shown below in Table II, where the activity and selectivity of the catalyst (B) are compared with the copper-zinc oxide catalyst of the prior art (A) (C-61-1) obtained from Catalyst and Chemicals Inc.) and a Catalyst prepared according to Example 1 (C) subjected to identical reaction conditions.

TABLE II

|  | gm-mols ACP/ hr/gm/cat. | gm-mols ACP/ hr/cc cat. | SELECTIVITY Mol % ACP Converted to EB @ % ACP Conversion | |
|---|---|---|---|---|
|  |  |  | @ 50% | @ 80% |
| (A) Cu/ZnO (prior art) | 0.046 | 0.065 | 4.4 | 11.8 |
| (B) Cu/Cr/Ba/Zn/Mg | 0.040 | 0.064 | 2.1 | 4.5 |
| (C) Cu/Cr/Ba/Zn | 0.040 | 0.067 | 3.0 | 6.4 |

It can be seen that the activity of the catalysts (B) and (C), while only slightly lower than that of the prior art (A), display a very much better selectivity to phenyl methyl carbinol and thus are substantially improved over the prior art catalyst (A) as indicated by the relatively small amount of ethyl benzene produced by catalysts (B) and (C). While the activity of the catalysts (B) and (C) are indicated to be similar to those of the prior art in this short duration batch experiment, it has been found in experiments carried out in continuous flow reactors that the catalysts (B) and (C) maintain a higher activity over a longer period of time than that of the copper-zinc oxide catalyst (A). Thus, the catalysts of the invention have a superior average activity and can be expected to remain operable for a substantially longer period than the catalyst of the prior art.

EXAMPLE 3

A catalyst (B) is prepared according to the method of Example 2 and has a composition of about 41 weight % CuO, 41.5 weight % Cr₂O₃, 8 weight % BaO, and 6.2 weight % ZnO and 0.83 weight % MgO. The catalyst is placed in a fixed basket autoclave (a continuous stirred-tank reactor) and subjected to continuous flow conditions at a temperature of about 155° C. and 84 kg/cm² gauge. The overall space velocity of the liquid is 10WHSV and about 7.6 mols of hydrogen are fed for each mol of acetophenone fed. The liquid feed contains about 37.8 weight % acetophenone, 49.2 weight % ethyl benzene, 6.9 weight % phenyl methyl carbinol, and 2.9 weight % styrene. After operation for 100 hours, the catalyst was removed from the reactor and its crush strength compared with the copper-zinc oxide catalyst of the prior art (A) (C-61-1 obtained from Catalyst and Chemicals Inc.), and a catalyst prepared according to Example 1 (C) both of which had been subjected to substantially the same process conditions. The measurements are shown in Table III below.

TABLE III

|  | Crush Strength, lbs | |
|---|---|---|
|  | Fresh | Used 100 Hours |
| (A) Cu/ZnO (prior art) | 27 | 8 |
| (B) Cu/Cr/Ba/Zn/Mg | 36 | 34 |
| (C) Cu/Cr/Ba/Zn | 50 | 35 |

It can be seen that even after the relatively short period of 100 hours exposure, the catalyst of the prior art has lost about two-thirds of its fresh crush strength. In contrast, catalyst (B) showed only a small decline, less than 10%, after 100 hours exposure and catalyst (C) declined, but still retained a high value. These results indicate clearly that there is a substantial improvement in the strength of the catalysts of the invention compared to the catalyst of the prior art.

The foregoing discussion of catalysts prepared according to the invention and their method of use is given for purposes of description and should not be considered to limit the scope of the invention, which is defined by the claims which follow.

What is claimed is:

1. A process for the hydrogenation of acetophenone to phenyl methyl carbinol by contacting said acetophenone with at least one mol of hydrogen for each mol of acetophenone over a fixed bed of catalyst pellets at temperatures in the range of about 50° C. to 200° C. and pressures in the range of about 20 kg/cm$^2$ gauge to 140 kg/cm$^2$ gauge wherein the composition of said catalyst pellets expressed as oxides consists essentially of: (a) a barium-copper chromite containing 30–55% by weight CuO, 30–57% by weight $Cr_2O_3$, and up to 16% by weight BaO; and (b) 1—13% by weight ZnO, relative to 100% by weight of said barium-copper chromite.

2. The process of claim 1 wherein said catalyst composition expressed as oxides includes 0.15–1.7% by weight MgO.

UNITED STATES PATENT AND TRADEMARK OFFICE
CERTIFICATE OF CORRECTION

PATENT NO. : 4,208,539
DATED : June 17, 1980
INVENTOR(S) : Jay A. Rashkin

It is certified that error appears in the above-identified patent and that said Letters Patent are hereby corrected as shown below:

Column 1, line 62 -- change "to" to -- in --;
Column 7, line 15 -- change "BB" to -- EB --;
           line 29 -- change "wieght" to -- weight --;
           line 30 -- change "Crhd2O_3" to -- $Cr_2O_3$ --;
           line 52 -- change "about" to -- above --.

Signed and Sealed this

Twenty-first Day of October 1980

[SEAL]

Attest:

SIDNEY A. DIAMOND

Attesting Officer     Commissioner of Patents and Trademarks